United States Patent [19]

Crews, Jr. et al.

[11] Patent Number: 4,926,694

[45] Date of Patent: May 22, 1990

[54] DELAMINATION TEST APPARATUS AND METHOD

[75] Inventors: John H. Crews, Jr., Grafton; James R. Reeder, Hampton, both of Va.

[73] Assignee: The United States of America as represented by the United States National Aeronautics and Space Administration, Washington, D.C.

[21] Appl. No.: 386,172

[22] Filed: Jul. 28, 1989

[51] Int. Cl.⁵ .............................................. G01N 3/00
[52] U.S. Cl. ...................................................... 73/794
[58] Field of Search ................. 73/794, 795, 799, 827, 73/831, 834, 835, 849, 852, 856, 150 A

[56] References Cited

U.S. PATENT DOCUMENTS

| | | | |
|---|---|---|---|
| 2,834,205 | 5/1958 | Pickup | 73/150 A |
| 3,026,721 | 3/1962 | Ensor et al. | 73/842 |
| 3,194,063 | 7/1965 | McKean | 73/852 |
| 3,354,704 | 11/1967 | Gloor | 73/796 |
| 3,580,065 | 5/1971 | Strittmater | 73/150 R |
| 4,566,335 | 1/1986 | Singhal | 73/849 |
| 4,589,288 | 5/1986 | Porter et al. | 73/852 |

FOREIGN PATENT DOCUMENTS

1317316  6/1987  U.S.S.R. .................................. 73/799

*Primary Examiner*—Robert Raevis
*Attorney, Agent, or Firm*—Harold W. Adams; John R. Manning; Charles E. B. Glenn

[57] ABSTRACT

A delamination test apparatus and method uses a single beam to simultaneously apply opening and shear stresses to a test specimen. A fulcrum extending downwardly from the beam produces shear stress in the specimen by downward movement, and opening stress by pivotal upward movement of the beam, which results by virtue of the fact that the applied load is on one side of the fulcrum while the test specimen is connected to the beam on the opposite side of the fulcrum.

12 Claims, 2 Drawing Sheets

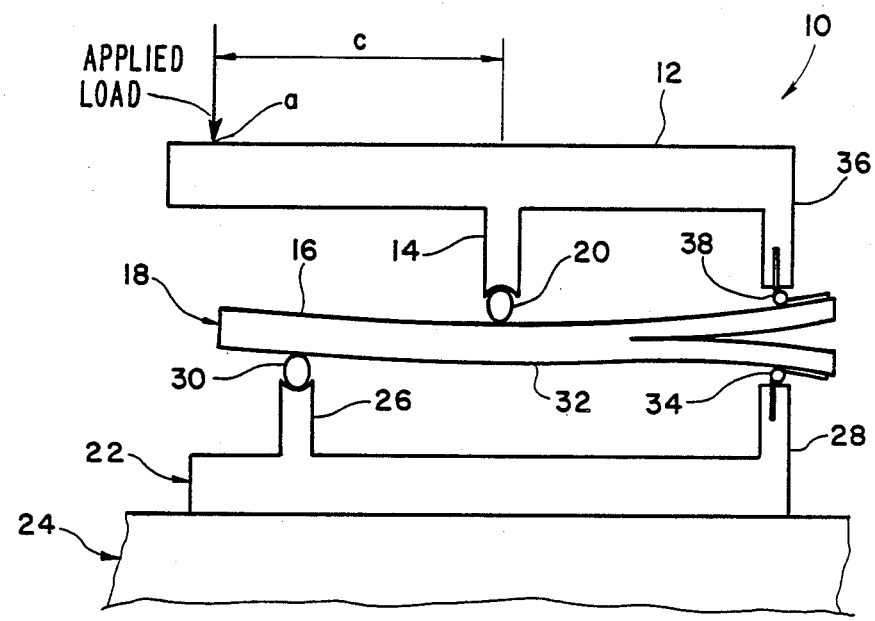
FIG. 1
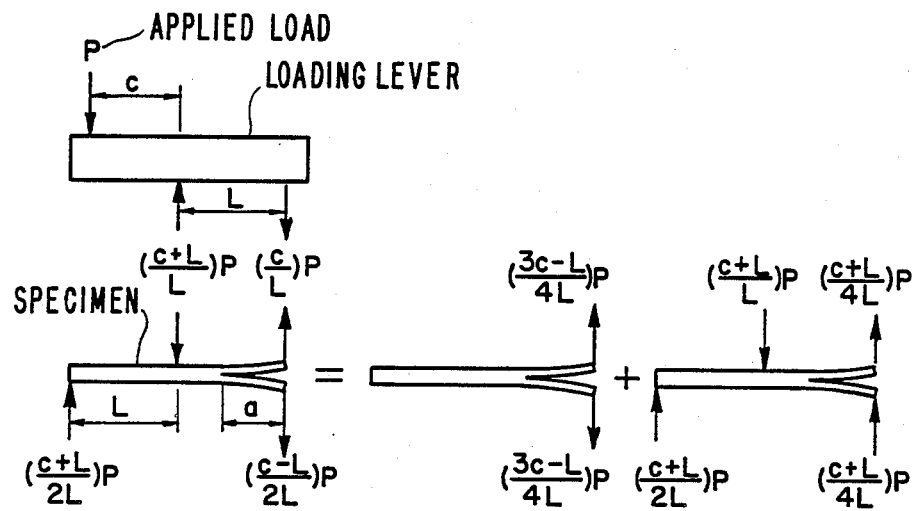
FIG. 2 (a)
MMB SPECIMEN
LOADING
FIG. 2 (b)
MODE I LOADING
FIG. 2 (c)
MODE II LOADING

DELAMINATION TEST APPARATUS AND METHOD

Origin of the Invention

The invention described herein was made by employees of the United States Government and may be manufactured and used by or for the Government for governmental purposes without the payment of any royalties thereon or therefor.

Background of the Invention

1. Field of the Invention

The present invention relates generally to materials testing and, more specifically, to an apparatus and method for testing delamination of materials by mixed mode bending.

2. Description of the Related Art

Composite structures are becoming more popular due to their high strength and low weight. A problem associated with these new materials is that failures in structural composites often develop as delamination between laminated plies. Typically, these delaminations initiate and grow as a result of combined peeling (or opening) stresses and sliding (or shear) stresses. Studies of delamination resistance should preferably account for the effects of combined opening and shear stresses, these stresses being referred respectively as mode I and mode II stresses.

Although most delamination tests are currently conducted using single-mode specimens, various mixed-mode test procedures have been used. These known procedures, however, have generally been met with one or more limiting drawbacks. An effective test apparatus and method has not heretofore been devised to simultaneously apply opening (mode I) loads and shear (mode II) loads while measuring the delamination resistance of a simple test piece.

One of the previously used mixed-mode delamination tests is referred to as the "edge delamination tension test". In this test, a laminated specimen is loaded in uniaxial tension until delaminations initiate at the specimen edge. A ply layup such as $(0/\pm 35/90)_S$ is used to produce high interlaminar edge stresses that cause delamination at the interface between the $-35$ degree and 90 degree plies. This method has several disadvantages. First of all, the delamination grows from an edge-stress singularity rather than from an initial delamination. Secondly, the ratio of mode I to mode II behavior at the delamination cannot be calculated by simple stress analysis methods. In addition, measurements are usually limited to delamination initiation because delamination size is difficult to monitor. Another problem is that different layups are required to produce different mode I/II ratios. It has also been found that transverse ply cracking can precede delamination and complicate the required stress analysis, and interlaminar thermal residual stresses can influence delamination and thus further complicate the stress analysis of the test specimen.

Another known test method is the "crack lap shear test." In this test, uniaxial loading is applied to one arm of a specimen containing an artificially introduced delamination referred to as a "split-laminate" specimen. The load transfer to the second arm causes mode I and II stresses at the delamination front as it grows. This approach has the following disadvantages: (1) the mode I/II ratio cannot be calculated by a simple close-form stress analysis, (2) different ply layups are required to produce different mode I/II ratios, and (3) only a narrow range of mode I/II ratios can be achieved.

Another known test procedure is the "mixed-mode flexure" test. In this test, a split-laminate specimen is bent by loading one arm. Load transfer between the two arms causes mode I and II stresses on the delamination plane. However, this test approach has a limited range of mode I/II ratios.

The Arcan specimen test is one in which a pre-cracked specimen is bonded to each half of a fixture that allows the specimen to be inclined relative to the uniaxial loading direction. The specimen orientation can be varied to produce different combinations of opening-mode and shear-mode loading on the delamination plane. However, the mode I/II ratio cannot be calculated by simple stress analysis procedures. Moreover, bond failures can limit the use of the method, especially for tough laminates.

Another known test is the asymmetric double cantilever beam (DCB) test, in which the end of a split-laminate specimen is fixed and its two arms are loaded in flexure using two different loads to produce mixed-mode loading on the delamination plane. This method allows a complete range of mode I/II ratios, but requires a complex testing system to simultaneously control the two applied loads.

In the "variable mixed-mode" test procedure, a split-laminate specimen is constrained on each end and subjected to an upward load on the upper arm of the specimen. This upward load pulls the two arms apart while bending the specimen and, hence, produces combined mode I and II loading on the delamination. This method has the disadvantage that the mode I/II ratio changes when the delamination grows.

A need exists for a simple mechanical structure for simultaneously applying mode I and Mode II stresses for delamination testing.

SUMMARY OF THE INVENTION

An object of the present invention is to provide a test apparatus for simultaneously applying opening and shear stresses in a test specimen to determine delamination characteristics of the specimen.

Another object of the present invention is to provide a test apparatus which applies mode I and mode II loads to a test specimen while measuring the delamination resistance thereof.

Another object of the present invention is to provide a test apparatus which is capable of varying the mode I/II ratio over a broad range.

Yet another object of the present invention is to provide an easily calculated mode I/II ratio by simple stress analysis procedures.

Another object of the present invention is to provide a test method for testing a laminated specimen, while providing a wide range of mode I/II ratios.

In a preferred embodiment of the present invention, an apparatus for testing a laminated composite specimen includes a base having two opposite ends, a first support extending upwardly from the base and movably supporting one end of the specimen, a second support extending upwardly from the base and being spaced from the first support and fixedly connected to the opposite end of the specimen at the lower surface thereof, a load applying beam having a fulcrum for abutment with the upper surface of the specimen at a point between the first and second supports, a third support extending from the beam and being fixedly connected to the opposite surface of the specimen at one end of the specimen, the second and third supports being substantially aligned, and means for applying a load to the beam at a point between the fulcrum and the opposite end of the beam, thereby simultaneously generating opening and shear stresses in the specimen.

These objects, together with other objects and advantages which will be subsequently apparent reside in the details of construction and operation of the apparatus as more fully hereinafter described and claimed, reference being had to the accompanying drawings forming a part thereof, wherein like reference numerals refer to like parts throughout.

BRIEF DESCRIPTION OF THE DRAWINGS

FIG. 1 is a schematic illustration of a first preferred embodiment of the present invention;

FIG. 2(a) is a schematic illustration showing mixed-mode bending specimen loading, and computational formulae for combined mode I and mode II loading;

FIG. 2(b) is a schematic illustration of mode I loading and formulae for the mode I component of loading;

FIG. 2(c) is a schematic illustration of mode II loading and formulae for the mode II component of loading;

DETAILED DESCRIPTION OF THE PREFERRED EMBODIMENTS

Figure 3:
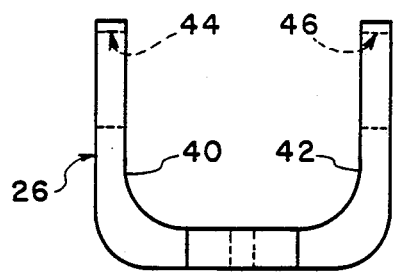
FIG. 3 is a front view of a mounting bracket or support for a roller used in the preferred embodiment illustrated in FIG. 1.

Referring now to FIG. 1, a delamination test apparatus is generally referred to by the numeral 10. The test apparatus 10 includes a loading beam 12 having a fulcrum 14 for abutment with an upper surface 16 of a test specimen 18. A distal end of the fulcrum 14 is provided with a roller 20 which engages the surface 16 and which is rotatable about an axis parallel to the surface 16.

A base 22 is supported on a stationary platform 24. First and second supports 26 and 28 extend upwardly from an upper surface of the base 22. Support 26 movably supports one end portion of the specimen 18 by means of a roller 30. Support 28 is spaced from the support 26 and is fixedly connected to the opposite delaminated end portion of the specimen at the lower surface 32 thereof. A piano hinge 34 has one portion connected to the support 28 by conventional means such as, for example, a clamp, while another portion of the hinge 34 is connected to the lower surface 32 a lower arm of the delaminated and of the specimen 18 by adhesive bonding or other suitable surface bonding techniques.

A support 36 extends downwardly from the loading beam 12 at one end thereof and is substantially aligned with the support 28. A second piano hinge 38 is used to connect the upper surface 16 of an upper arm of the delaminated end portion. of the specimen 18 to the support 36. One portion of the piano hinge 38 is connected to the support 36 by conventional means such as, for example, a clamp, while the other portion is adhesively bonded to the upper surface 16. The hinges 34 and 38 have horizontal pivot axes which lie in a substantially vertical plane.

When a load is applied to the loading beam 12 at the point "a", the loading beam 12 simultaneously applies a downward, bending force through the fulcrum 14 and roller 20, and an upward, opening force.

The upward opening load on the right end of FIG. 1 is similar to that used in a double cantilever beam test for mode I delamination. The downward load is similar to that used in the end-notch flexure test for mode II delamination. These loads can be applied simultaneously by the present apparatus to thereby produce combined mode I and II delamination in the test specimen.

As shown in the schematic illustration of FIG. 1, the combined loading on the test specimen 18 is achieved by applying a single load to the loading beam 12. The applied load may be provided by a hydraulic ram or other standard test machinery. A pivotal joint may be provided between the ram and the loading beam 12. When the beam 12 is loaded in the downward direction, the center roller 20 loads the specimen downwardly and, simultaneously, the right end of the specimen is loaded upwardly. These two loads are proportioned to the applied load and their relative magnitudes can be changed by varying the loading distance "c." Such variation of c produces a wide range of mode I/II ratios for mixed-mode delamination testing.

The mode I and II loading on the specimen 18 can be expressed in terms of the applied load which can be measured using a conventional test machine. Then, simple equations which are known for double cantilever beam (DCB) specimen testing and for end-notch flexure (ENF) specimen testing can be used to resolve the measured mixed-mode response into its mode I and II components. For example, mixed-mode delamination toughness can be determined by measuring the applied load during an increment of delamination growth, and then resolved into its mode I and II components. Also, these simple equations for pure mode I and II testing allow the loading distance c to be selected to produce desired mode I/II test ratios.

The present invention has a significant advantage over the known methods described herein in that the individual mode I and mode II delamination contributions in the test specimen can be analyzed using simple beam-theory equations, thus eliminating the need for a time-consuming, difficult numerical analysis. Also, the present invention allows a wider range of mode I/II ratios than possible with many of the previously described methods. The present invention also allows mixed-mode delamination tests to be conducted in conventional laboratory test machines, in that the apparatus can be placed between a stationary base and a movable ram associated with an existing test apparatus. Another advantage of the present invention is that it allows the mode I/II ratio to be held at a constant value during delamination growth, unlike the variable mixed-mode test described previously.

The loading beam 12 is preferably an aluminum I beam, which is several orders of magnitudes stiffer than the specimen and thus is assumed to be rigid. The beam load, the mid-span load, and the left support reaction are applied through bearing-mounted rollers to reduce frictional forces. The right end of the specimen is loaded through high-quality, extruded aluminum hinges bonded to the specimen "arms" (which are the two portions of the specimen above and below a dividing notch or un-bonded region). The specimen may be for example a 24 ply graphite/PEEK uni-directional laminate, 25 mm wide and 102 mm long.

FIG. 2(a) shows the mixed-mode bending (MMB) loading expressed in terms of the applied load P, the loading lever length c, and the specimen half-span L. As shown in FIG. 2(b), the mode I component of this loading is $$P_1 = \frac{(3c - L)}{4L} P$$

Delamination resistance is usually expressed in terms of the critical value of strain energy release rate (G) for the test specimen when the specimen loading causes the delamination to extend. Simple beam theory analysis of the double cantilever beam (DCB) specimen leads to $$G_I = \frac{12a^2 P_1^2}{b^2 h^3 E_{11}} \tag{1}$$

where $G_I$ is the mode I strain energy release rate, a is delamination length, b is specimen width, h is half-thickness, and $E_{11}$ is the specimen longitudinal modulus. Substituting for $P_I$ leads to the following equation for $G_I$ of the MMB test.

$$G_I = \frac{3a^2 P^2}{4b^2 h^3 L^2 E_{11}} (3c - L)^2 \tag{2}$$

FIG. 2(c) shows the mode II portion of the MMB loading. The right end loading has been divided equally between the two equal-stiffness arms of the specimen. This is equivalent to the conventional loading of the end-notch flexure (ENF) test. For the MMB test, the mode II bending load is $$P_{II} = \frac{(c + L)P}{L}$$

as shown in FIG. 2(c). The following equation for $G_{II}$ of the ENF test was presented by A.J. Russell in "On the Measurement of Mode II Interlaminar Fracture Energies," *DREP Materials Report*, 82-0, Dec. 1982.

$$G_{II} = \frac{9a^2 P_{II}^2}{16 b^2 h^3 E_{11}} \tag{3}$$

Substituting for $P_{II}$ the corresponding equation for $G_{II}$ of the MMB test is $$G_{II} = \frac{9a^2 P^2}{16 b^3 h^3 L^2 E_{11}} (c + L)^2 \tag{4}$$

By dividing equation (2) by equation (4), the $G_I/G_{II}$ ration for the MMB test can be expressed as $$G_I/G_{II} = \frac{4 [(3c - L)]^2}{3 [c + L]^2} \quad c \geq \frac{L}{3} \tag{5}$$

$G_I/G_{II}$ is only a function of load position c and half-span length L. The $G_I/G_{II}$ ratio is zero for $c = L/3$, and equation (5) is invalid for smaller c values because this model does not account for contact between the two arms of the specimen. The total strain energy release rate for the MMB test is obtained by adding equations (2) and (4).

$$G = \frac{3a^2 P^2}{16 b^2 h^3 L^2 E_{11}} [4(3c - L)^2 + 3(c + L)^2] \tag{6}$$

The various components illustrated schematically in FIG. 1 need not be described in great detail since the structure is relatively simple. However, in a preferred embodiment, the supports 26, 28 and 36, as well as the fulcrum 14 are mounting brackets which can be connected to either the base or the load applying beam by threaded fasteners, for example.

Figure 4:
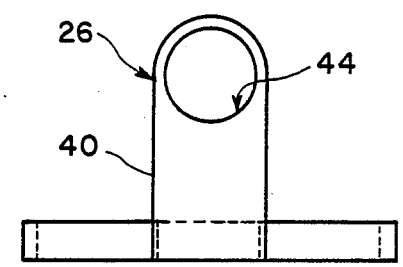
FIG. 4 is a side elevational view of the mounting bracket of FIG. 3.
Figure 5:
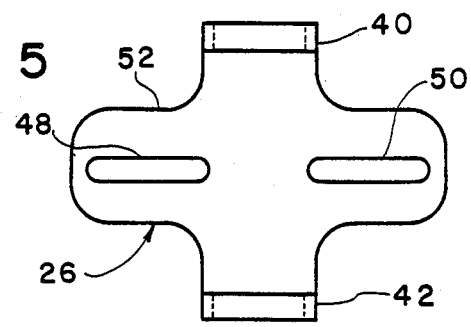
FIG. 5 is a top plan view of the mounting bracket of FIG. 3.

FIGS. 3 through 5 illustrate support 26 (which would be identical to fulcrum 14), which includes a pair of spaced apart, upstanding arms 40 and 42. The arms 40 and 42 are provided with a pair of aligned bores 44 and 46, respectively, which receive bearings (not shown). A roller is rotatably mounted between the two arms. Mounting slots 48 and 50 provided in a base portion 52 of the support used for mounting the base portion to the base 22.

Figure 6:
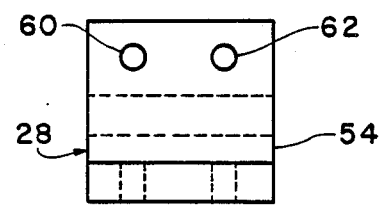
FIG. 6 is a front view of a mounting bracket for holding one of the hinge portions described schematically in FIG. 1.
Figure 7:
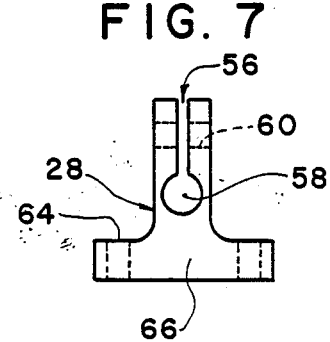
FIG. 7 is a side elevational view of the mounting bracket of FIG. 6.

FIGS. 6 and 7 illustrate support 28 (which would be identical to support 36). The support 28 is essentially a clamp for holding half of a piano hinge. A vertically upstanding portion 54 is provided with an axial slot 56 which extends downwardly into the upstanding portion 54 and terminates in an enlarged, circular opening 58. A flat portion of the piano hinge is fitted into the slot 56 and is clamped therein by passing threaded fasteners through transverse bores 60 and 62. Bores 64 are also provided on a base portion 66 to facilitate attachment of the support 28 to the base 22.

The many features and advantages of the present invention are apparent from the detail specification, and, thus, it is intended by the appended claims to cover all such features and advantages of the mixed mode bending delamination test apparatus and method which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. An apparatus for testing a laminated composite specimen having upper and lower opposite surfaces and first and second ends, said second end being delaminated forming oppositely disposed lower and upper arms on said second end comprising:
   a base having two opposite ends;
   a first support extending upwardly from the base and movably supporting said first end of the specimen;
   a second support extending upwardly from the base and being spaced from the first support and fixedly connected to the lower arm of said second end of the specimen;
   a load applying beam having first and second ends and a fulcrum for abutment with the upper surface of the specimen at a point between the first and second supports;
   a third support extending from said second end of said beam and being fixedly connected to the upper arm of the specimen at said second end of the specimen, the second and third supports being substantially aligned; and means for applying a load to the beam at a point between the fulcrum and the first end of the beam thereby simultaneously generating opening and shear stresses in the specimen to increase the delamination at said second end.

2. An apparatus according to claim 1, wherein the first support has a distal end and a support roller mounted at the distance end for rotatably supporting said first end of the specimen.

3. An apparatus according to claim 2, wherein the second support has a distal end, and first means for connecting the second support to the surface of said lower arm at said second end of the specimen.

4. An apparatus according to claim 3, wherein the first connecting means is a hinge.

5. An apparatus according to claim 3, wherein the third support has a distal end, and second means for connecting the third support to the surface of said upper arm of the specimen.

6. An apparatus according to claim 5, wherein the second connecting means is a hinge.

7. An apparatus according to claim 1, wherein the fulcrum has a distal end and a fulcrum roller mounted at the distal end.

8. An apparatus according to claim 1, wherein the first support is positionally adjustable along the base.

9. A mixed-mode method of testing a laminated composite specimen for delamination resistance, said specimen being delaminated at one end forming oppositely disposed lower and upper arms comprising:

placing the test specimen on a base;
connecting the lower arm of the test specimen to one end of the base;
juxtaposing a beam over the test specimen with a fulcrum of the beam in contact with a surface of the test specimen opposite the base;
connecting the beam to the upper arm of the test specimen opposite the base or one side of the fulcrum; and
applying a downward load to the beam on an opposite side of the fulcrum to simultaneously generate opening and shear stresses in said specimen until said delamination increases, the value of said downward load applied to said beam when said delamination increases being a measure of the resistance of said specimen to delamination.

10. A method according to claim 9, further comprising varying the distance between the fulcrum and the applied load to the beam to thereby vary the ratio of opening stress to shear stress.

11. An apparatus for testing a laminated composite specimen having upper and lower opposite surfaces and delaminated at one end forming oppositely disposed lower and upper arms comprising:

a base having two opposite supports thereon for supporting the specimen thereon;
a load applying beam having opposing ends and a fulcrum therebetween for abutment with the upper surface of the specimen at a point between the two opposite supports on;
means for connecting said lower arm of the specimen to one of said supports and said upper arm to a corresponding end of said beam; and
means for applying a load to the beam at a point between the opposite end of the beam and the fulcrum, thereby simultaneously generating opening and shear stress in the specimen to increase the delamination thereby testing the resistance of said specimen to delamination.

12. An apparatus according to claim 11, wherein the connecting means comprises a pair of hinges.

* * * * *